(12) United States Patent
Bonrath et al.

(10) Patent No.: US 8,124,804 B2
(45) Date of Patent: Feb. 28, 2012

(54) PROCESS FOR THE ACYLATION OF ORGANIC HYDROXY COMPOUNDS

(75) Inventors: Werner Bonrath, Freiburg (DE); Valentina Pasquinelli, Turin (IT)

(73) Assignee: DSM IP Assets B.V., Heerlen (NL)

( * ) Notice: Subject to any disclaimer, the term of this patent is extended or adjusted under 35 U.S.C. 154(b) by 60 days.

(21) Appl. No.: 12/521,017

(22) PCT Filed: Dec. 19, 2007

(86) PCT No.: PCT/EP2007/011145
§ 371 (c)(1), (2), (4) Date: Jun. 24, 2009

(87) PCT Pub. No.: WO2008/077543
PCT Pub. Date: Jul. 3, 2008

(65) Prior Publication Data
US 2010/0048945 A1    Feb. 25, 2010

(30) Foreign Application Priority Data
Dec. 27, 2006   (EP) .................................... 06026904

(51) Int. Cl.
   C07C 67/02 (2006.01)
(52) U.S. Cl. ........................................ 560/249; 560/255
(58) Field of Classification Search .................... None
   See application file for complete search history.

(56) References Cited

FOREIGN PATENT DOCUMENTS
JP         49-055633 A    *   5/1974

OTHER PUBLICATIONS

White et al, Basic Energy Sciences Advisory Committee Subpanel Workshop Report, Opportunities for Catalysis in the 21st Century, 2002, pp. 1-47.*
International Search Report for PCT/EP2007/011145, mailed Jun. 9, 2008.
Written Opinion of the International Searching Authority for PCT/EP2007/011145, mailed Jun. 9, 2008.
Posner, Okada, Babiak, Miura, Rose: "Organic Reactions at Alumina Surfaces: An Extremely Simple, Mild and Convenient Method for Acetylating Primary Alcohols", Synthesis, vol. 10, 1981, pp. 789-790, XP00248011.
Posner, Oda: "Organic Reactions at Alumina Surfaces. An Extremely Simple, Convenient and Selective Method for Acetylating Primary Alcohols in the Presence of Secondary Alcohols" Tetrahedron Letters, vol. 22. No. 50, 1981, pp. 5003-5006, XP002480812.
Yadav Babu: "Reactions on a Solid Surface. A Simple, Economical and Efficient Acylation of Alcohols and Amines over A1203", Journal of Organic Chemistry, vol. 69, 2004, pp. 577-580, XP002480813.
Rana, Barlow, Matta: "The Selective Acetylation of Primary Alcohols in the Preence of Secondary Alcohols in Carbohydrates", Tetrahedron Letter, vol. 22, No. 50, 1981, pp. 5007-5010.
"Alpha-Tocopherol Acetate Prepn—by Acetylation of Alpha-Tocopherol in Presence of Inorg. Solid Acids", Derwent, 1975, XP002292233.

* cited by examiner

*Primary Examiner* — Paul A Zucker
(74) *Attorney, Agent, or Firm* — Nixon & Vanderhye P.C.

(57) ABSTRACT

A process for acylating organic hydroxy compounds, characterized in that the acylation is effected in the presence of a metal oxide which does not carry a catalyst and the use of such metal oxides for acylating organic hydroxy compounds.

7 Claims, No Drawings

PROCESS FOR THE ACYLATION OF ORGANIC HYDROXY COMPOUNDS

This application is the U.S. national phase of International Application No. PCT/EP2007/011145, filed 19 Dec. 2007, which designated the U.S. and claims priority to Europe Application No. 06026904.0, filed 27 Dec. 2006, the entire contents of each of which are hereby incorporated by reference.

The present invention is concerned with a novel process for the acylation of organic hydroxy compounds and the use of metal oxides therein.

Acylations, especially acetylations, are important reactions in organic chemistry, useful in the preparation of commercially valuable products and of intermediates in such processes. Several processes have been developed to perform this type of reaction in an efficient manner, with or without different catalysts, the majority being carried out in the presence of acid catalysts.

WO 2004/096790 describes the preparation of tocyl or tocopheryl acylates with an acylating agent in the presence of a catalyst of the formula $HCR^1R^2R^3$, wherein the substituents $R^1$-$R^3$ represent sulpho- or perfluoroalkylsulfonyl groups. While acidic catalysts accelerate the reaction and reduce reaction time considerably they are known to induce certain side reactions, e.g., water-eliminations from tertiary alcohols, and attack centers of asymmetry, thus influencing stereochemistry unfavorably. Basic catalysts which do not show these disadvantages are normally less effective because of longer reaction times. WO 2004/096791 discloses the acylation of tocopherols with an acylating agent in the presence of a solid heterogeneous Bronstedt acid catalyst on a solid carrier wherein the solid carrier comprises silicon dioxide and/or titanium dioxide and/or organofunctional polysiloxanes. Such carriers are commercially available, e.g., under the trade mark AEROLYST®, from Degussa AG, Germany.

WO 2005/103026 describes the manufacture of tocopheryl acylates by reacting a tocopherol with an acylating agent in the presence of solid basic catalysts containing alkali and/or alkaline earth metals on $SiO_2$ or $Al_2O_3$.

While acid-catalysed acylations often yield undesired side-products by elimination reactions, e.g., of water, especially in the case of tertiary alcohols, base-catalysed acylations normally do not show these disadvantages, however, need more time to reach high yields. Therefore, there is still a need for efficient acylation methods with a main focus on reduction of waste, high yields and short reaction times. It has now surprisingly been found that organic hydroxy compounds can be effectively acylated, i.e. in high yields and with great selectivity, in short reaction times, in the presence of metal oxides without any specific acidic or basic compounds used as catalysts on such carriers. These metal oxides can replace the catalysts used so far in acylation reactions: they can be used several times (several recycles) without essential loss of activity and are easier to regenerate. In some cases good yields (more than 50%) were obtained already after 30 minutes' reaction time; in other cases nearly quantitative results were obtained after 2-6 hours. Such metal oxides without an amount of a specific catalyst have so far not been used as catalysts in acylating reactions of organic hydroxy compounds.

The present invention, therefore, relates to a process for acylating organic hydroxy compounds which process is characterized in that the acylation is effected in the presence of a metal oxide, viz. a metal oxide which does not carry a catalyst. The invention further relates to the use of such metal oxides, viz. metal oxides which are normally the solid carrier only for a catalyst, in a process for acylating organic hydroxy compounds and to the acylated hydroxy compounds thus obtained.

The term "organic hydroxy compounds" used herein covers all organic compounds having a hydroxy group which is amenable to acylation. Such compounds are aliphatic, alicyclic, aromatic and araliphatic compounds, i.e., alcohols and phenols, carrying one or more, e.g., two, three, four, etc. hydroxy groups and include polyalcohols and polyphenols. Aliphatic alcohols are primary, secondary and tertiary alcohols which may be straight- or branched-chain, saturated or unsaturated, i.e., with one or more carbon-carbon double and/or triple bond(s). The aromatic alcohols, viz. phenols, may be carbocyclic and/or heterocyclic compounds of monocyclic or condensed nature, viz. may contain two, three or more cycles. The hydroxy compounds have preferably 1-50 carbon atoms. Examples of unsaturated aliphatic hydroxy compounds are nerol, geraniol, phytol and farnesol; allylic alcohols, e.g. 2-propen-1-ol, especially tert.-allylic alcohols, such as, linalool, nerolidol and isophytol; 2-propin-1-ol and dehydrolinalool. Of specific interest within this group are those compounds which have applications as flavorings or fragrances and are parts of perfumes, among which are many mono- and bicyclic monoterpenes (C10-compounds), e.g., borneol, menthols, terpineols, fenchols and thujols; and phenols, e.g., thymol (or p-cymenol). Within the terpenoid or isoprenoid compound group there are hydroxy compounds belonging to the sesquiterpenes (C15), diterpenes (C20), triterpenes (C30) and tetraterpenes (C40). Representatives of triterpenes are calciferols and of tetraterpenes carotenoids. Isoprenoid alcohols with more than 4 isoprenyl residues, i.e., having 25, 30, 35, 40, 45, 50, etc., carbon atoms are known as polyprenols and are also covered by the term "hydroxy compound(s)". Another group of "hydroxy compounds" of specific interest within the present invention are tocopherols. The term "tocopherol" as used herein is to be understood to refer to any compound derived from the basic structure of tocol [2-methyl-2-(4',8',12'-trimethyltridecyl)-6-chromanol], having a free 6-hydroxy group and exhibiting vitamin E activity, viz. any tocopherol having the saturated side chain 4',8',12'-trimethyltridecyl, such as $\alpha$-, $\beta$-, $\gamma$-, $\delta$-, $\zeta_2$- or $\eta$-tocopherol, and also any tocotrienol having three double bonds in the side chain [4',8',12'-trimethyltridec-3',7',11'-trienyl], such as $\epsilon$- or $\zeta_1$-tocopherol. Of these various tocopherols (all-rac)-$\alpha$-tocopherol, generally referred to as vitamin E, is of primary interest, being the most active and industrially most important member of the vitamin E group.

The metal oxides used in the acylation process of the present invention are oxides or mixtures of oxides normally used as solid carriers for different kinds of catalysts. Examples of such catalysts, without limitation, are $SiO_2$, all kinds of silicates, silica gels, diatomaceous earth or zeolites, $Al_2O_3$, $TiO_2$, $ZrO_2$ and $ZnO_2$ which can be used separately or in combination with each other. They are commercially available or can be prepared in accordance with methods well-known in the art. Among the metal oxides use of which is preferred in the present invention are mixtures on the basis of two or three of the above-mentioned products, especially of $SiO_2$, $Al_2O_3$ and $TiO_2$. Among the commercially available solid carriers for catalysts those from Degussa AG, Hanau, Germany, known under the registered trade mark Aerolyst®, e.g., AEROLYST® 7750, AEROLYST® 7751 and AEROLYST® 7752 are most preferred. The solid carriers for catalysts are known to have high pore volume and large specific surface. The pore volume is in the range of 0.1-2.0 ml/g, preferably 0.7 ml/g and the BET surface is in the range of 10-800 $m^2$/g.

The acylation can be carried out in principle using any acylating agent conventionally used for the acylation of aliphatic or aromatic, viz. phenolic hydroxy groups present in the above-defined hydroxy compounds. Especially suitable types of such acylating agents are acid anhydrides and acyl halides. The acyl groups in such acylating agents may be derived from aliphatic carboxylic acids, e.g. from linear or branched chain alkanoic acids, in particular from $C_{1-7}$-alkanoic acids such as acetic acid, propionic acid, butyric acid and pivalic acid, or from higher alkanoic acids (fatty acids) with up to 20 carbon atoms such as palmitic acid; or from aromatic carboxylic acids, particularly benzoic acid, so that in each case the appropriate acylate, being an alkanoate, or e.g. the benzoate, respectively, of the hydroxy compound is produced in the acylation process. Examples of aliphatic acyl halides are linear or branched chain alkanoyl chlorides such as acetyl, propionyl and butyryl chloride, and, of aromatic acyl halides, benzoyl chloride. Anhydrides are normally preferred because it is generally an advantage to avoid the use of halogen compounds as acylating agents. The most preferred acylating agent is acetic anhydride.

The acylation in accordance with the process of the present invention may by carried out batchwise or in a continuous process, in the presence or in the absence of an added solvent, but preferably one of the reactants, i.e. the hydroxy compound or the acylating agent, is used in excess and no additional solvent is used. Preferably, the acylating agent is used in excess, preferably in a one- to about a threefold molar amount, more preferably in a 1.5- to 2.5-fold molar amount, and most preferably in a 1.75- to 2.25-fold molar amount, relative to the molar amount of the hydroxy compound present in the initial reaction mixture. If an additional solvent is used, however, this is suitably a polar or non-polar aprotic organic solvent, particularly an aliphatic, preferably $C_{4-10}$-aliphatic, hydrocarbon, e.g. pentane, hexane, heptane or decane; an alicyclic, preferably $C_{4-7}$-alicyclic, hydrocarbon, e.g. cyclohexane; or an aromatic, particularly $C_{6-10}$-aromatic, hydrocarbon, e.g. benzene, toluene, an xylene or naphthalene.

In a preferred embodiment of the invention the solid metal oxide is added to the reaction mixture in pure solid form without further activation or modification. The amount of oxide used is based on the amount of the reactant, i.e. the hydroxy compound or the acylating agent, usually the former, which is used in the lesser molar amount and is suitably in the range from about 0.005 to about 15 mmol, preferably from about 0.01 to about 1.0 mmol, based on said lesser molar amount, when the process is effected in a batchwise operational mode. For the alternative continuous operational mode, the relative amount of catalyst will have to be adjusted to the size of the reactor and the flow rates of the reactants. In this case it will be appreciated that the determination of the appropriate relative amount based on the figures for the batchwise operational mode is within the normal skill of the production chemist.

The acylation process in accordance with the present invention is conveniently carried out at temperatures from about 80° C. to about 120° C., preferably from about 90° C. to about 110° C.

Moreover, the process is conveniently carried out under an inert gas atmosphere, preferably under gaseous nitrogen or argon, especially the former.

The progress of the reaction is suitably monitored by analytical means, such as gas chromatography of samples taken from the reaction mixture at various time intervals during the reaction.

After completion of the acylation the produced acylated hydroxy compound can be isolated by distilling off, preferably under reduced pressure, the excess acylating agent, and the secondary product formed in the acylation, e.g., acetic acid when acetic anhydride is used as the acylating agent, followed by further distillation, also preferably under reduced pressure, to collect as pure a fraction of the desired acylation product as required.

The acylation process of the present invention is illustrated in more detail by the following Examples.

General

All reactions were carried out under argon. Commercially available (all-rac)-α-tocopherol (97.8%), linalool (97.7%), isophytol (96.2%), dehydro-linalool (98%) and 3-methyl-pent-1-en-4-yn-3-ol (98%) were used without further purification. The solid basic catalysts were used without further activation or modification. The crude products were analyzed by GC (area %).

EXAMPLE 1

Acylation of (all-rac)-α-tocopherol

In a 50 ml four-necked flask equipped with a glass propeller stirrer, thermometer, and reflux condenser with an argon inlet, 16.74 g (38 mmol) of (all-rac)-α-tocopherol were dissolved in 7.61 ml (79.8 mmol) of acetic anhydride in the presence of 0.5 g of catalyst. The flask was placed in a hot oil bath of 100° C. Every 30 minutes, 3 drops of the reaction mixture were dissolved in 1.5 ml of cyclohexane, neutralized with sodium acetate, filtrated and analyzed by GC (area %).

Analytics:

| Instrument: | HP 6850 gas chromatograph with split injector and FID HP 6850 auto sampler | |
|---|---|---|
| | Data acquisition and reporting, HP ChemStation | |
| Inlet | Split ratio | 25:1 |
| | Injector temperature | 250° C. |
| | Injection volume | 1 μl |
| Column | Stationary phase | HP-5 |
| | Length × diameter | 30 m × 320 μm; Film 0.25 μm |
| | Column material | Fused silica |
| | Producer | Agilent |
| | Initial flow | 1.4 ml/min |
| | Mode | Constant flow |
| Column temperature | 100° C. (0 min) → 10° C./min → 320° C. (10 min). Total 32 min | |
| Front Detector | Detector temperature: | 320° C. |
| | Makeup Gas type | Helium | 25 ml/min |
| | | Hydrogen flow | 30 ml/min |
| | | Air flow | 400 ml/min |

TABLE 1

Synthesis of all-(rac)-α-tocopherylacetate with AEROLYST ® 7750 and recycle

| Time [h] | TocoAc, fresh catalyst [Area %] | TocoAc (1. recycle) [Area %] | TocoAc (2 rec.) [Area %] |
|---|---|---|---|
| 0.5 | 67.12 | 91.99 | 48.2 |
| 1.0 | 89.28 | 95.42 | 81.6 |
| 1.5 | 93.71 | 96.33 | 88.3 |
| 2.0 | 95.49 | 96.66 | 89.0 |
| 2.5 | 96.35 | 97.04 | 89.6 |
| 3.0 | 96.68 | 97.12 | 89.9 |
| 3.5 | 97.07 | 97.26 | 90.2 |
| 4.0 | 97.06 | 97.32 | 90.7 |

TABLE 1-continued

Synthesis of all-(rac)-α-tocopherylacetate with AEROLYST ® 7750 and recycle

| Time [h] | TocoAc, fresh catalyst [Area %] | TocoAc (1. recycle) [Area %] | TocoAc (2 rec.) [Area %] |
|---|---|---|---|
| 4.5 | 97.06 | 97.49 | 91.0 |
| 5.0 |  | 97.62 | 91.5 |
| 5.5 |  | 97.63 | 92.0 |
| 6.0 |  | 97.81 | 92.1 |

TABLE 2

Synthesis of all-(rac)-α-tocopherylacetate with AEROLYST ® 7751 and recycle

| Time [h] | TocoAc (fresh cat.) [Area %] | TocoAc (1. recycle) [Area %] | TocoAc (2. recycle) [Area %] | TocoAc (3. recycle) [Area %] | TocoAc (4. recycle) [Area %] | TocoAc (5. recycle) [Area %] |
|---|---|---|---|---|---|---|
| 0.5 | 94.05 | 62.6 | 85.2 | 59.8 | 72.5 | 50.3 |
| 1 | 96.29 | 91.5 | 93.6 | 84.5 | 89.8 | 77.3 |
| 1.5 | 97.04 | 94.8 | 95.5 | 90.9 | 93.7 | 86.6 |
| 2 | 97.25 | 95.8 | 96.1 | 93.4 | 95.2 | 91.1 |
| 2.5 | 97.35 | 96.6 | 96.5 | 94.5 | #N/A | 92.9 |
| 3 | 97.58 | 96.8 | 96.6 | 95.2 | 96.5 | 94.1 |
| 3.5 | 97.60 | 97.0 | 96.9 | 95.9 | 96.9 | 94.9 |
| 4 | 97.70 | 97.3 | 97.1 | 96.1 | 97.3 | 95.4 |
| 4.5 |  | 97.4 | 97.1 | 96.5 | 97.2 | 95.8 |
| 5 |  | 97.1 | 97.5 | 96.7 | 97.4 | 96.1 |
| 5.5 |  | 97.5 | 97.4 | 96.6 | 97.4 | 96.6 |
| 6 |  | 97.3 | 97.5 | 97.0 | 97.5 | 96.6 |

TABLE 3

Synthesis of all-(rac)-α-tocopherylacetate with AEROLYST ® 7752 and recycle

| Time [h] | TocoAc (fresh cat.) [Area %] | TocoAc (1. recycle) [Area %] | TocoAc (2. recycle) [Area %] | TocoAc (3. recycle) [Area %] | TocoAc (4. recycle) [Area %] | TocoAc (5. recycle) [Area %] |
|---|---|---|---|---|---|---|
| 0.5 | 97.73 | 38.04 | 88.7 | 94.9 | 80.9 | 41.3 |
| 1.0 | 97.76 | 81.50 | 95.8 | 96.9 | 91.5 | 65.6 |
| 1.5 | 97.75 | 89.15 | 97.3 | 97.1 | 94.1 | 77.9 |
| 2.0 | 97.82 | 92.25 | 97.5 | #N/A | 95.3 | 84.0 |
| 2.5 | 97.89 | 93.81 | 97.6 | 97.5 | 95.9 | 87.8 |
| 3.0 | 97.88 | 94.80 | 97.5 | 97.7 | 96.3 | 90.4 |
| 3.5 | 97.83 | 95.70 | 97.3 | 97.6 | #N/A | 92.1 |
| 4.0 | 97.83 | 95.52 | 97.7 | 97.9 | 96.9 | 93.2 |
| 4.5 |  | 96.30 | #N/A | 97.7 | 96.9 | 93.9 |
| 5.0 |  | 96.28 | 97.8 | 97.8 | 97.1 | 94.4 |
| 5.5 |  | 96.84 | 97.8 | 97.8 | 97.2 | 95.0 |
| 6.0 |  | 97.08 | 97.9 | 97.6 | 97.2 | 95.5 |

EXAMPLE 2

In a 50 ml four-necked flask equipped with a glass propeller stirrer, thermometer and reflux condenser with an argon inlet, 11.4 g (76 mmol) of linalool were dissolved in 15.22 ml (158.6 mmol) of acetic anhydride in the presence of 1.0 g of catalyst. The flask was placed in a hot oil bath of 100° C. Every 30 minutes, 3 drops of the reaction mixture were dissolved in 1.5 ml of cyclohexane, neutralized with sodium acetate, filtrated and analysed by GC (area %).

Analytics:

| Instrument: | HP 5890 gas chromatograph with split injector and FID HP 5890 auto sampler Data acquisition and reporting, HP ChemStation |
|---|---|
| Inlet | Split ratio 50:1 |
|  | Injector temperature 250° C. |
|  | Injection volume 1 μl |
| Column | Stationary phase Optima-delta 3 |
|  | Length × diameter 30 m × 320 μm; Film 0.25 μm |
|  | Column material Fused silica |
|  | Producer Macherey Nagel |
|  | Mode Constant flow |
| Column temperature | 60° C. (0 min) → 8° C./min → 300° C. (2 min). Total 32 min |
| Front Detector | Detector temperature: 300° C. |

TABLE 4

Synthesis of linalylacetate with zinc aluminate 2.1 eq Ac₂O, batch-experiment,

| Time [h] | Linalool [Area %] | Linalylacetate [Area %] | Geranylacetate [Area %] | Nerylacetate [Area %] |
|---|---|---|---|---|
| 0.5 | 94.7 | 3.2 | 0.0 | 0.0 |
| 1.0 | 91.3 | 6.5 | 0.0 | 0.0 |
| 1.5 | 88.3 | 9.5 | 0.1 | 0.0 |

TABLE 4-continued

Synthesis of linalylacetate with zinc aluminate
2.1 eq Ac$_2$O, batch-experiment,

| Time [h] | Linalool [Area %] | Linalylacetate [Area %] | Geranylacetate [Area %] | Nerylacetate [Area %] |
|---|---|---|---|---|
| 2.0 | 85.4 | 12.2 | 0.1 | 0.0 |
| 2.5 | 82.8 | 14.7 | 0.2 | 0.0 |
| 3.5 | 77.8 | 19.2 | 0.3 | 0.1 |
| 4.0 | 75.3 | 21.4 | 0.3 | 0.2 |
| 4.5 | 73.3 | 23.4 | 0.4 | 0.2 |
| 5.0 | 71.1 | 25.2 | 0.4 | 0.3 |
| 5.5 | 69.2 | 26.9 | 0.5 | 0.3 |
| 6.0 | 67.3 | 28.7 | 0.6 | 0.3 |

TABLE 5

Synthesis of linalylacetate with AEROLYST ® 7750
2.1 eq Ac$_2$O, batch-experiment

| Time [h] | Linalol [Area %] | Linalylacetate [Area %] | Geranylacetate [Area %] | Nerylacetate [Area %] |
|---|---|---|---|---|
| 0.5 | 8.4 | 26.6 | 12.8 | 2.8 |
| 1.0 | 1.3 | 11.3 | 19 | 4.3 |
| 1.5 | 0.4 | 5.8 | 20.6 | 17.4 |
| 2.0 | 0.2 | 3.2 | 21.3 | 12.7 |

TABLE 6

Synthesis of linalylacetate with AEROLYST ® 7751
2.1 eq Ac$_2$O, batch-experiment

| Time [h] | Linalol [Area %] | Linalylacetate [Area %] | Geranylacetate [Area %] | Nerylacetate [Area %] |
|---|---|---|---|---|
| 0.5 | 5.4 | 21.8 | 15.3 | 3.6 |
| 1.0 | 0.6 | 7.1 | 20.4 | 4.9 |
| 1.5 | 0.1 | 2.6 | 21.2 | 4.9 |

TABLE 7

Synthesis of linalylacetate with AEROLYST ® 7752
2.1 eq Ac$_2$O, batch-experiment

| Time [h] | Linalol [Area %] | Linalylacetate [Area %] | Geranylacetate [Area %] | Nerylacetate [Area %] |
|---|---|---|---|---|
| 0.5 | 3.5 | 17.9 | 16.0 | 3.5 |
| 1.0 | 0.3 | 4.0 | 20.8 | 4.9 |
| 1.5 | 0.0 | 0.9 | 21.4 | 5.1 |
| 2.0 | 0.0 | 0.3 | 22.3 | 5.5 |

EXAMPLE 3

In a 50 ml four-necked flask, equipped with a glass propeller stirrer, thermometer and reflux condenser with an argon inlet, 11.25 g (38 mmol) of isophytol were dissolved in 7.61 ml (79.8 mmol) of acetic anhydride in the presence of 0.5 g of catalyst. The flask was placed in an oil bath of 100° C. Every 30 minutes, 3 drops of the reaction mixture were dissolved in 1.5 ml of cyclohexane, neutralized with sodium acetate, filtrated and analyzed by GC (area %).

Analytics:

| Instrument: | HP 6850 gas chromatograph with split injector and FID HP 6850 auto sampler Data acquisition and reporting, HP ChemStation | |
|---|---|---|
| Inlet | Split ratio | 25:1 |
| | Injector temperature | 250° C. |
| | Injection volume | 1 μl |
| Column | Stationary phase | HP-5 |
| | Length × diameter | 30 m × 530 μm; Film 3 μm |
| | Column material | Fused silica |
| | Producer | Agilent |
| | Initial flow | 1.4 ml/min |
| | Mode | Constant flow |
| Column temperature | 100° C. (0 min) → 10° C./min → 320° C. (10 min). Total 32 min | |
| Front Detector | Detector temperature: | 320° C. |
| | Makeup Gas type Helium | 25 ml/min |
| | Hydrogen flow | 30 ml/min |
| | Air flow | 400 ml/min |

TABLE 8

Synthesis of isophytylacetate with zinc aluminate
2.1 eq Ac$_2$O, batch-experiment

| Time [h] | Isophytol [Area %] | Isophytylacetate [Area %] |
|---|---|---|
| 0.5 | 94.8 | 2.1 |
| 1.0 | 91.4 | 4.6 |
| 1.5 | 88.9 | 7.0 |
| 2.0 | 87.3 | 9.2 |
| 3.0 | 82.6 | 12.8 |
| 3.5 | 80.6 | 14.7 |
| 4.0 | 78.5 | 16.5 |
| 4.5 | 77.9 | 18.1 |
| 5.0 | 75.1 | 19.7 |
| 5.5 | 73.4 | 21.3 |
| 6.0 | 71.6 | 22.6 |

TABLE 9

Synthesis of isophytylacetate with AEROLYST ® 7750
2.1 eq Ac₂O, batch-experiment

| Time [h] | Isophytol [Area %] | Isophytylacetate [Area %] | Total [Area %] |
|---|---|---|---|
| 0.5 | 8.5 | 33.9 | 42.4 |
| 1.0 | 0.8 | 19.8 | 20.6 |
| 1.5 | 0.1 | 9.0 | 9.1 |

TABLE 10

Synthesis of isophytylacetate with AEROLYST ® 7751
2.1 eq Ac₂O, batch-experiment

| Time [h] | Isophytol [Area %] | Isophytylacetate [Area %] | Total [Area %] |
|---|---|---|---|
| 0.5 | 7.4 | 30.6 | 38.0 |
| 1.0 | 0.5 | 14.7 | 15.2 |
| 1.5 | 0.1 | 4.7 | 4.8 |
| 2.0 | 0.1 | 1.6 | 1.7 |
| 2.5 | 0.1 | 0.7 | 0.8 |

TABLE 11

Synthesis of isophytylacetate with AEROLYST ® 7752
2.1 eq Ac₂O, batch-experiment

| Time [h] | Isophytol [Area %] | Isophytylacetate [Area %] | Total [Area %] |
|---|---|---|---|
| 0.5 | 11.3 | 36.2 | 47.5 |
| 1.0 | 1.5 | 24.6 | 26.1 |
| 1.5 | 0.3 | 13.4 | 13.7 |
| 2.0 | 0.1 | 6.6 | 6.7 |

EXAMPLE 4

In a 50 ml four-necked flask equipped with a glass propeller, thermometer and reflux condenser with an argon inlet, 11.56 g (76 mmol) of dehydrolinalool were dissolved in 15.22 ml (158.6 mmol) of acetic anhydride in the presence of 1.0 g of catalyst. The flask was placed in a hot oil bath of 100° C. Every 30 minutes, 3 drops of the reaction mixture were dissolved in 1.5 ml of cyclohexane, neutralized with sodium acetate, filtrated and analyzed by GC (area %).

Analytics:

| Instrument: | HP 5890 gas chromatograph with split injector and FID |
| | HP 5890 auto sampler |
| | Data acquisition and reporting, HP ChemStation |
| Inlet | Split ratio 50:1 |
| | Injector temperature 250° C. |
| | Injection volume 1 µl |
| Column | Stationary phase Optima-delta 3 |
| | Length × diameter 30 m × 320 µm; Film 0.25 µm |
| | Column material Fused silica |
| | Producer Macherey Nagel |
| | Mode Constant flow |
| Column temperature | 60° C. (0 min) → 8° C./min → 300° C. (0 min). Total 30 min |
| Front Detector | Detector temperature: 300° C. |

TABLE 12

Synthesis of dehydrolinalylacetate with zinc aluminate
2.1 eq Ac₂O, batch-experiment

| Time [h] | Dehydrolinalool [Area %] | Dehydrolinalylacetate [Area %] | Total [Area %] |
|---|---|---|---|
| 0.5 | 96.6 | 2.9 | 99.5 |
| 1.0 | 93.4 | 6.1 | 99.5 |
| 1.5 | 90.7 | 8.8 | 99.5 |
| 2.5 | 85.4 | 14.1 | 99.5 |
| 3.0 | 83.0 | 16.6 | 99.6 |
| 3.5 | 80.8 | 18.8 | 99.6 |
| 4.0 | 78.5 | 21.1 | 99.6 |
| 4.5 | 76.4 | 23.2 | 99.6 |
| 5.0 | 74.3 | 25.3 | 99.6 |
| 5.5 | 72.4 | 27.2 | 99.6 |
| 6.0 | 70.4 | 29.1 | 99.5 |

TABLE 13

Synthesis of dehydrolinalylacetate with AEROLYST ® 7750

| Time [h] | DLLAc (I experiment) [Area %] | DLLAc (I recycle) [Area %] | DLLAc (II recycle) [Area %] | DLLAc (III recycle) [Area %] | DLLAc (IV recycle) [Area %] | DLLAc (V recycle) [Area %] |
|---|---|---|---|---|---|---|
| 0.5 | 93.4 | 62.9 | 29.5 | 10.7 | 15.6 | 7.7 |
| 1 | 95.1 | 90.3 | 67.8 | 29.1 | 46.9 | 20.6 |
| 1.5 | 94.4 | 95.4 | 85.2 | 50.7 | 67.3 | 39.9 |
| 2 | 94.0 | 96.5 | #N/A | 67.5 | 76.1 | 56.9 |
| 2.5 | | 96.9 | 95.1 | #N/A | 81.8 | #N/A |
| 3 | | 97.0 | 96.7 | 79.4 | 86.3 | 79.8 |
| 3.5 | | | 96.9 | 89.3 | 92.0 | 85.2 |
| 4 | | | 96.9 | 92.3 | #N/A | 88.6 |
| 4.5 | | | 97.8 | 93.9 | 94.1 | 90.9 |
| 5 | | | 97.0 | 95.0 | 95.3 | 92.6 |
| 5.5 | | | 97.3 | #N/A | 96.1 | 94.7 |
| 6 | | | 97.1 | 97.7 | 96.2 | 94.4 |

TABLE 14

Synthesis of dehydrolinalylacetate with AEROLYST ® 7751

| Time [h] | DLLAc (I experiment) [Area %] | DLLAc (I recycle) [Area %] | DLLAc (II recycle) [Area %] | DLLAc (III recycle) [Area %] | DLLAc (IV recycle) [Area %] | DLLAc (V recycle) [Area %] |
|---|---|---|---|---|---|---|
| 0.5 | 87.2 | 36.9 | 27.7 | 14.2 | 17.5 | 9.3 |
| 1 | 93.1 | 84.9 | 69.3 | 45.7 | 47.4 | 24.7 |
| 1.5 | 94.1 | 94.3 | 87.0 | 73.2 | 69.4 | 44.4 |
| 2 | 94.5 | 95.8 | 93.5 | 85.7 | #N/A | 60.9 |
| 2.5 | | 97.1 | 91.6 | #N/A | 89.7 | 71.5 |
| 3 | | 96.2 | 96.5 | 95.6 | 92.6 | 79.6 |
| 3.5 | | | 97.3 | 96.7 | 95.2 | #N/A |
| 4 | | | | 97.1 | 95.8 | 88.4 |
| 4.5 | | | | 97.1 | 96.5 | 90.8 |
| 5 | | | | 97.2 | 97.3 | 92.8 |
| 5.5 | | | | 97.6 | 97.2 | 93.8 |
| 6 | | | | 97.8 | 97.4 | 94.8 |

TABLE 15

Synthesis of dehydrolinalylacetate with AEROLYST ® 7752

| Time [h] | DLLAc (I experiment) [Area %] | DLLAc (I recycle) [Area %] | DLLAc (II recycle) [Area %] | DLLAc (III recycle) [Area %] | DLLAc (IV recycle) [Area %] | DLLAc (V recycle) [Area %] |
|---|---|---|---|---|---|---|
| 0.5 | 93.8 | 32.3 | 21.9 | 13.6 | 10.8 | 10.5 |
| 1 | 93.3 | 84.8 | 61.0 | 43.7 | 31.4 | 28.2 |
| 1.5 | 93.3 | 93.9 | 82.8 | 69.4 | 54.3 | 47.8 |
| 2 | 93.1 | #N/A | 91.9 | 83.1 | 71.6 | 65.6 |
| 2.5 | | 96.3 | 95.4 | 90.1 | 81.3 | 76.1 |
| 3 | | 96.0 | 96.1 | #N/A | #N/A | 82.9 |
| 3.5 | | 95.9 | #N/A | 95.2 | 87.2 | 87.8 |
| 4 | | 96.6 | 96.6 | 96.0 | 94.1 | 92.8 |
| 4.5 | | | 97.5 | 96.6 | 94.8 | 93.8 |
| 5 | | | 97.1 | 96.6 | 95.7 | 95.6 |
| 5.5 | | | 97.5 | 96.7 | 96.3 | 95.6 |
| 6 | | | | 96.8 | 96.7 | 96.2 |

EXAMPLE 5

In a 50 ml four-necked flask equipped with a glass propeller, thermometer and reflux condenser with an argon inlet, 7.3 g (76 mmol) of 3-methylpent-1-en-4-yn-3-ol were dissolved in 15.22 ml (158.6 mmol) of acetic anhydride in the presence of 1.0 g of catalyst. The flask was placed in a hot oil bath of 100° C. Every 3 minutes, 3 drops of the reaction mixture were dissolved in 1.5 ml of cyclohexane, neutralized with sodium acetate, filtrated and analyzed by GC (area %).
Analytics:

TABLE 16

Synthesis of 3-pentylacetate with zinc aluminate
2.1 eq Ac$_2$O, batch-experiment

| Time [h] | 3-Pentol [Area %] | 3-Pentylacetate [Area %] | Total [Area %] |
|---|---|---|---|
| 0.5 | 96.2 | 3.8 | 100.0 |
| 1.0 | 91.6 | 8.4 | 100.0 |
| 1.5 | 87.7 | 12.3 | 100.0 |

| Instrument: | HP 6890 gas chromatograph with split injector and FID | |
| | HP 6890 auto sampler | |
| | Data acquisition and reporting, HP ChemStation | |
| Inlet | Split ratio | 12.5:1 |
| | Injector temperature | 200° C. |
| | Injection volume | 1 µl |
| Column | Stationary phase | Optima-1 |
| | Length × diameter | 30 m × 530 µm; Film 3 µm |
| | Column material | Fused silica |
| | Producer | Macherey Nagel |
| | Initial flow | 3.4 ml/min |
| | Mode | Constant flow |
| Column temperature | 50° C. (0 min) → 5° C./min → 90° C. (0 min) 40° C./min → 300° C. (6.8 min). Total 20.05 min | |
| Front Detector | Detector temperature: | 300° C. |
| | Makeup Gas type | Helium |
| | | 45 ml/min |
| | Hydrogen flow | 40 ml/min |
| | Air flow | 450 ml/min |

TABLE 16-continued

Synthesis of 3-pentylacetate with zinc aluminate
2.1 eq Ac₂O, batch-experiment

| Time [h] | 3-Pentol [Area %] | 3-Pentylacetate [Area %] | Total [Area %] |
|---|---|---|---|
| 2.0 | 84.0 | 16.0 | 100.0 |
| 2.5 | 79.6 | 19.8 | 99.4 |

TABLE 17

Synthesis of 3-pentylacetate with AEROLYST ® 7750
2.1 eq Ac₂O, batch-experiment

| Time [h] | 3-Pentol [Area %] | 3-Pentylacetate [Area %] | 1-Pentylacetate (E + Z) [Area %] | Total [Area %] |
|---|---|---|---|---|
| 0.5 | 5.3 | 56.6 | 28.7 | 90.6 |
| 1.0 | 0.0 | 48.0 | 42.8 | 90.8 |
| 1.5 | 0.0 | 42.1 | 48.5 | 90.6 |
| 2.0 | 0.0 | 41.6 | 46.8 | 88.4 |

TABLE 18

Synthesis of 3-pentylacetate with AEROLYST ® 7751
2.1 eq Ac₂O, batch-experiment

| Time [h] | 3-Pentol [Area %] | 3-Pentylacetate [Area %] | 1-Pentylacetate (E + Z) [Area %] | Total [Area %] |
|---|---|---|---|---|
| 0.5 | 5.1 | 52.8 | 30.4 | 88.3 |
| 1.0 | 0.0 | 43.4 | 46.7 | 90.1 |
| 1.5 | 0.0 | 38.8 | 51.3 | 90.1 |
| 2.0 | 0.0 | 36.4 | 53.7 | 90.1 |

TABLE 19

Synthesis of 3-pentylacetate with AEROLYST ® 7752
2.1 eq Ac₂O, batch-experiment

| Time [h] | 3-Pentol [Area %] | 3-Pentylacetate [Area %] | 1-Pentylacetate (E + Z) [Area %] | Total [Area %] |
|---|---|---|---|---|
| 0.5 | 2.5 | 49.1 | 37.8 | 89.4 |
| 1.0 | 0.0 | 40.9 | 49.6 | 90.5 |
| 1.5 | 0.0 | 37.4 | 51.2 | 88.6 |

The invention claimed is:

1. A process for acylating organic hydroxy compounds which comprises effecting acylation of the organic hydroxy compounds with an acid anhydride in the absence of an additional solvent and in the presence of a metal oxide which does not carry a catalyst, wherein the metal oxide is at least one oxide selected from the group consisting of $SiO_2$, $Al_2O_3$, $TiO_2$, $ZrO_2$ and $ZnO_2$.

2. The process of claim 1, wherein the hydroxy compound is an aliphatic, aromatic or araliphatic alcohol.

3. The process of claim 1, wherein the hydroxy compound is an aliphatic $C_{1-50}$ alcohol which has a straight or branched carbon chain and may contain one or more double and/or triple bonds.

4. The process of claim 1, wherein the anhydride is an aliphatic or aromatic carboxylic acid anhydride.

5. The process of claim 1, wherein the hydroxy compound comprises 1-10isoprenyl units.

6. The process of claim 1, wherein the hydroxy compound is a terpenoid.

7. The process of claim 1, wherein the hydroxy compound is a tocopherol.

* * * * *